US008785133B2

(12) United States Patent
Parida et al.

(10) Patent No.: US 8,785,133 B2
(45) Date of Patent: Jul. 22, 2014

(54) OLIGONUCLEOTIDES AND PROCESS FOR DETECTION OF SWINE FLU VIRUS

(75) Inventors: Manmohan Parida, Gwalior (IN); Jyoti Shukla, Gwalior (IN); Santhosh Sannarangiah, Gwalior (IN); Sashi Sharma, Gwalior (IN); Venkata Lakshmana Putcha Rao, Gwalior (IN); Rajagopalan Vijayaraghavan, Gwalior (IN)

(73) Assignee: Defence Research & Development Organisation, New Delhi (IN)

( * ) Notice: Subject to any disclaimer, the term of this patent is extended or adjusted under 35 U.S.C. 154(b) by 0 days.

(21) Appl. No.: 13/509,535

(22) PCT Filed: Nov. 11, 2010

(86) PCT No.: PCT/IN2010/000734
§ 371 (c)(1),
(2), (4) Date: May 11, 2012

(87) PCT Pub. No.: WO2011/058580
PCT Pub. Date: May 19, 2011

(65) Prior Publication Data
US 2012/0231445 A1    Sep. 13, 2012

(30) Foreign Application Priority Data
Nov. 12, 2009  (IN) ............................ 2329/DEL/2009

(51) Int. Cl.
*C12Q 1/68*    (2006.01)
*C07H 21/00*   (2006.01)

(52) U.S. Cl.
USPC ...................... 435/6.12; 536/24.33; 536/24.3

(58) Field of Classification Search
None
See application file for complete search history.

(56) References Cited

U.S. PATENT DOCUMENTS 8,043,813 B2 * 10/2011 Minekawa et al. .......... 435/6.12

OTHER PUBLICATIONS

Imai et al., (Development of H5-RT-LAMP (loop-mediated isothermal amplification) system for rapid diagnosis of H5 avian influenza virus infection, Vaccine 24 (2006) 6679-6682).*
NCBI Accession No. CY047715 (Oct. 15, 2009).*
Buck et al. (Biotechniques. 1999. 27(3): pp. 528-536).*
Lowe et al. (Nucleic Acids Research, vol. 18, No. 7, p. 1757-1761, 1990).*
Tomita et al. (Loop-mediated isothermal amplification (LAMP) of gene sequences and simple visual detection of products, Nature Protocols, vol. 3, No. 5, 2008).*
PrimerExplorer, available at http://primerexplorer.jp/e/, Jul. 6, 2007.*

Kubo et al. (Development of a Reverse Transcription-Loop-Mediated Isothermal Amplification Assay for Detection of Pandemic (H1N1) 2009 Virus as a Novel Molecular Method for Diagnosis of Pandemic Influenza in Resource-Limited Settings, Journal of Clinical Microbiology, p. 728-735, col. 48, No. 3, Mar. 2010).*
NCBI Accession No. FJ966082 (Apr. 27, 2009).*
CDC Centers for Disease Control and Prevention, Interim guidance for the Detection of Novel Influenza A Virus Using Rapid Influenza Diagnostic Tests, http://www.cdc.gov/h1n1flu/guidance/rapid_testing.htm, published Aug. 10, 2009; accessed Mar. 18, 2013.
http://www.who.int/csr/resources/publications/swineflu/CDCrealtimeRTPCRprotocol_20090428.pdf.
Carr et al., "Development of a real-time RT-PCR for the detection of Swine-lineage Influenza A (H1N1) virus infections," *Journal of Clinical Virology*, 45:196-199, 2009.
CDC Centers for Disease Control and Prevention, Interim guidance for the Detection of Novel Influenza A Virus Using Rapid Influenza Diagnostic Tests, http://www.cdc.gov/h1n1flu/guidance/rapid_testing.htm.
Chen et al., "Development of reverse transcription loop-mediated isothermal amplification for rapid detection of H9 avian influenza virus," *Journal of Virological Methods*, 151:200-203, 2008.
Dong et al., "Detection of human novel influenza A (H1N1) viruses using multi-fluorescent real-time RT-PCR," *Virus Research*, 147:85-90, 2010.
Gu et al., "Rapid and specific detection of H3 swine influenza virus using reverse transcription loop-mediated isothermal amplification method," *Journal of Microbiology*, 108:1145-1154, 2010.
He et al., "Rapid Multiplex Reverse Transcription-PCR Typing of Influenza A and B Virus, and Subtyping of Influenza A Virus into H1, 2, 3, 5, 7, 9, N1 (Human), N1 (Animal), N2, and N7, Including Typing of Novel Swine Origin Influenza A (H1N1) Virus during the 2009 Outbreak in Milwaukee, Wisconsin," J. Clin. Microbial, 47(9):2772, 2009.
Imai et al., "Rapid diagnosis of H5N1 avian influenza virus infection by newly developed influenza H5 hemagglutinin gene-specific loop-mediated isothermal amplification method," *Journal of Virological Methods*, 141:173-180, 2007.
International Preliminary Report on Patentability for PCT/IN2010/000734, dated May 15, 2012.
International Search Report and Written Opinion for PCT/IN2010/000734, dated Jan. 4, 2011.
Pabbaraju et al., "Design and Validation of Real-Time Reverse Transcription-PCR Assays for Detection of Pandemic (H1N1) 2009 Virus," *J. Clin. Microbiol.*, 47(11):3454, 2009.
Panning et al., "Detection of Influenza A(H1N1)v Virus by Real-Time RT-PCR," *Eurosurveillance*, 14:36, 2009.
Wenzel et al., "Library of Prefabricated Locked Nucleic Acid Hydrolysis Probes Facilitates Rapid Development of Reverse-Transcription Quantitative Real-Time PCR Assays for Detection of Novel Influenza," *Clinical Chemistry*, 55:12:2218-2222, 2009.
http://www.who.int/csr/resources/publications/swineflu/CDCrealtimeRTPCRprotocol_20090428.pdf, Apr. 28, 2009.

* cited by examiner

Primary Examiner — Christopher M Babic
Assistant Examiner — Aaron Priest
(74) Attorney, Agent, or Firm — Cooley LLP

(57) ABSTRACT

A process of detection of pandemic swine flu virus H1N1 type in a sample is provided herein. Also provided are highly specific oligonucleotides useful for rapid detection of swine flu virus in a sample, as well as swine flu virus specific isothermal gene amplification assay for early clinical diagnosis of H1N1 human patients.

8 Claims, 1 Drawing Sheet

SEQUENCE LISTING

```
<160> NUMBER OF SEQ ID NOS: 8

<210> SEQ ID NO 1
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 1
aagctcagca aatcctaca                                           19

<210> SEQ ID NO 2
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 2
tccctcactt tgggtctt                                            18

<210> SEQ ID NO 3
<211> LENGTH: 25
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 3
gactttgttg gtcagcacta gtaga                                    25

<210> SEQ ID NO 4
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 4
aaagggaaag aagtcctcg                                           19

<210> SEQ ID NO 5
<211> LENGTH: 25
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 5
```

```
tctatcagaa tgcagatgca tatgt                                              25

<210> SEQ ID NO 6
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 6
tgctatttcc ggcttgaa                                                      18

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 7
gatggtgaat gccccatagc                                                    20

<210> SEQ ID NO 8
<211> LENGTH: 23
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 8
ttgtggggtc atcaagatac agc                                                23
```

OLIGONUCLEOTIDES AND PROCESS FOR DETECTION OF SWINE FLU VIRUS

FIELD OF INVENTION

Figure 1:
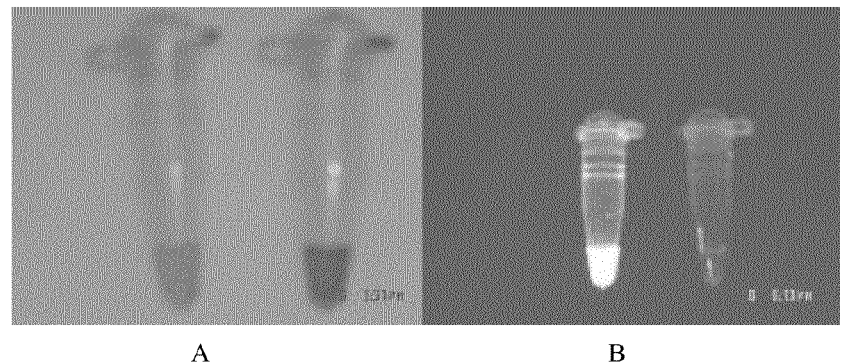

The present invention relates to quick and sensitive assay for detection of Swine Flu Virus.

BACKGROUND OF THE INVENTION

The 2009 Swine Flu pandemic was caused by a new strain of H1N1 influenza A virus that had not been recognized previously in pigs or humans, although six of its eight gene segments were similar to ones previously detected in triple reassortant swine influenza viruses in pigs in North America. The strain represents a quadruple reassortment of two swine strains, one human strain, and one avian strain of influenza. The largest proportion of genes comes from swine influenza viruses (30.6 percent from North American swine influenza strains, 17.5 percent from Eurasian swine influenza strains), followed by North American avian influenza strains (34.4 percent) and human influenza strains (17.5 percent). Pigs play an important role in interspecies transmission of influenza virus. Susceptible pig cells possess receptors for both avian (alpha 2-3-linked sialic acids) and human influenza strains (alpha 2-6-linked sialic acids), which allow for the reassortment of influenza virus genes from different species if a pig cell is infected with more than one strain.

A typical feature of newly emergent pandemic influenza strains is that severe infection occurs disproportionately in individuals who are not at the extremes of age. In contrast, seasonal influenza is more likely to cause severe disease in infants, young children, and elderly individuals. The virus can be spread amongst humans from direct contact which can occur through coughing, sneezing or contamination of hands and surfaces. The severity of symptoms is highly variable, although with most people suffering only relatively mild symptoms. Patients are considered contagious for up to a week after the onset of symptoms but children may be contagious for longer periods of time. Influenza virus is present in respiratory secretions of infected persons. As a result, influenza virus can be transmitted through sneezing and coughing via large-particle droplets. Transmission via contact with surfaces that have been contaminated with respiratory droplets or by aerosolized small-particle droplets may also occur, although these modes of transmission have not been proven. In addition to respiratory secretions, certain other bodily fluids (e.g., diarrheal stool) should also be considered potentially infectious.

The signs and symptoms of influenza caused by pandemic H1N1 influenza A virus are similar to those of seasonal influenza, although gastrointestinal manifestations appear to be more common with pandemic H1N1 influenza A. The severity appears to be less than what was observed during the influenza pandemic of 1918 to 1919. The most common clinical findings of the 2009 H1N1 influenza A pandemic have been fever, cough, sore throat, malaise and headache; vomiting and diarrhea have also been common, both of which are unusual features of seasonal influenza. Other frequent findings have included chills, myalgias, and arthralgias. Both leukocytosis and leucopenia have been observed among hospitalized patients in Mexico, many hospitalized patients have had leucopenia, elevated aminotransferases, elevated lactate dehydrogenase, and elevated creatinine phosphokinase. Some patients have also had renal insufficiency.

To establish the diagnosis of pandemic H1N1 influenza A, an upper respiratory sample (nasopharyngeal swab, nasal swab, throat swab, combined oropharyngeal/nasopharyngeal swab, or nasal aspirate) should be collected. A confirmed case of pandemic H1N1 influenza A is defined as an individual with an ILI with laboratory-confirmed pandemic H1N1 influenza A virus detection by real-time reverse transcriptase (RT)-PCR or culture.

Recommendations on whom to test may differ by state or community. Not all individuals with suspected pandemic H1N1 influenza A need to have the diagnosis confirmed, particularly if the illness is mild or the person resides in the area of confirmed cases. The recommended test to confirm the diagnosis of pandemic H1N1 influenza A virus is real-time reverse transcriptase (RT)-PCR for influenza A, B, H1, and H3 (He J, Bose M E, Beck E T, Fan J, Tiwari S, Metallo J: Rapid multiplex reverse transcription-PCR typing of influenza A and B virus, and subtyping of influenza A virus into H1, 2, 3, 5, 7, 9, N1 (human), N1 (animal), N2, and N7, including typing of novel swine origin influenza A (H1N1) virus, during the 2009 outbreak in Milwaukee, Wis. J. Clin. Microbiol. 2009, 47:2772-2778). However, in some regions of the country, RT-PCR is performed only when the results will substantially impact clinical management or when there is a recognized public health benefit. The strain of H1N1 influenza A virus associated with the 2009 pandemic tests positive for influenza A and negative for H1 and H3 by real-time RT-PCR. Isolation of pandemic H1N1 influenza A virus using culture is diagnostic, but culture is usually too slow to help guide clinical management. A negative viral culture does not exclude pandemic H1N1 influenza A infection. Clinicians may consider using rapid influenza antigen tests as part of their evaluation of patients suspected of having pandemic H1N1 influenza A, but results should be interpreted with caution (Dong H, Zhang Y, Xiong H: Detection of human novel influenza A (H1N1) viruses using multi-fluorescent real-time RT-PCR. Virus Res 2009, 147(1):85-90).

Rapid-Test Sensitivity for Novel Swine-Origin Influenza A (H1N1) Virus in Humans There are various diagnostic tests are available in the prior art, however the problem with these tests are that these tests do not provide accurate result and provides too many false negative and/or positive results. The tests known in the art fails to detect known swine flu in laboratory conditions leading in negative results. Thus, till date there are no tests that actually guarantee that whether Swine flue virus is present or absent in a sample obtained from a patient. This is important because the patients at higher risk that really need the medication might not be treated due to false negative results. Therefore, there is a need to provide a rapid method for detection of swine flu which is highly sensitive and specific enabling early differential diagnosis from other seasonal Flu viruses having similar clinical symptoms.

A confirmed case of pandemic H1N1 influenza A can be made through real-time reverse transcription polymerase chain reaction RTPCR or culture. The recommended test to confirm the diagnosis of pandemic H1N1 influenza A virus is real-time RTPCR for influenza A, B, H1, and H3. Isolation of pandemic HINT influenza A virus using culture is diagnostic, but culture is usually too slow to help guide clinical management.

A large number of real-time RTPCR tests have been reported with different chemistry and multiplexing formats (Wenzel J J, Walch H, Bollwein M, Niller H H, Ankenbauer W, Mauritz R, Höltke H J: Library of prefabricated locked nucleic acid hydrolysis probes facilitates rapid development of reverse-transcription quantitative real-time PCR assays for detection of novel influenza A/H1N1/09 virus. Clin Chem 2009, 55(12):2218-22; Panning M, Eickmann M, Landt O: Detection of influenza A(H1N1)v virus by real-time RT-PCR. Euro Surveill 2009, 10; 14(36): iii-19329; Pabbaraju K, Wong S, Wong A A: Design and validation of real-time reverse transcription-PCR assays for detection of pandemic (H1N1) 2009 virus. J Clin Microbiol 2009, 47(11):3454-60). However in the current pandemic scenario, the only validated CDC real-time RTPCR (CDC protocol of real-time RTPCR for influenza A (H1N1). Geneva: World Health Organization (2009) Available at: http://www.who.int/csr/resources/publications/swineflu/CDC Real-time RTPCR protocol Swine H1 Ass-2009_20090428.pdf. Acesses 2009 Jul. 20) is approved by WHO for confirmation of pandemic novel swine origin H1N1 infection. This CDC real-time RTPCR is based on a panel of oligonucleotide primers and dual labeled hydrolysis probe employing Invitrogen Superscript™ III Platinum® one step quantitative kit with four sets of primer and probes for Universal Influenza A, Swine Influenza A, Swine H1(New H1N1), House Keeping gene (RNase P) for testing the quality of RNA template.

One of the limitations of the existing WHO approved CDC real-time RTPCR is that the test system is very expensive considering the large number of primer and probe sets employed. In addition, the requirement of expensive real-time PCR instrument also restricts its application only to few referral laboratories with good financial resources. Over all, real-time RTPCR test system is expensive and time consuming as it requires 3-4 hours. Consequently real-time RTPCR is not the method of choice in basic clinical settings in developing countries for clinical diagnosis of novel S-OIV due to the requirement of sophisticated instrumentation and expensive reagents (Carr M J, Gunson R, Maclean A: Development of a real-time RT-PCR for the detection of swine-lineage influenza A (H1N1) virus infections. J Clin Virol 2009, 45(3): 196-199).

It is therefore critical to develop simple and economical molecular tests that can be used in field conditions especially at peripheral healthcare settings as a routine test without requirement of any sophisticated high end instruments.

OBJECTS OF THE INVENTION

One object of the present invention is to provide a field based gene amplification technique that can be used in a routine diagnostic laboratory as well as in peripheral health care centers for early clinical diagnosis of novel H1N1 Swine Flue virus in acute phase human patient serum samples.

Another object of the present invention is to provide highly sensitive and specific oligonucleotides to identify and pick up very low copy number of the novel H1N1 Swine Flu virus RNA and high degree of specificity enabling early differential diagnosis from other seasonal Flu viruses having similar clinical symptoms.

Another object of the present invention is to provide a rapid and reliable process for detection and identification of novel H1N1 Swine Flue virus at early stage of disease.

Further object of the present invention is to provide a simple and inexpensive process for detection as well as identification of novel H1N1 Swine Flu virus without requiring any sophisticated detection equipments at any stage.

SUMMARY OF THE INVENTION

One aspect of the present invention provides an oligonucleotide set for detection of Swine Flue Virus H1 type in a sample, the set comprises the oligonucleotides as set forth in SEQ ID NO: 3 to SEQ ID NO: 8.

Another aspect of the present invention provides a process for detecting Swine flu virus H1 type in a sample, the process comprises providing a sample, mixing the sample with the oligonucleotides as set forth in SEQ ID NO: 3 to SEQ ID NO: 8 and buffer comprising reagents used for DNA amplification to obtain a reaction mixture, incubating the reaction mixture at a substantial temperature for a substantial period of time and detecting amplified product, wherein presence of the amplified products confirms presence of the virus.

Yet another aspect of the present invention is to provide a process of detecting of Swine Flu Virus H1 type in a sample, wherein the process comprises providing a sample, obtaining cDNA from the sample using oligonucleotides as set forth in SEQ ID NO: 1 and SEQ ID NO: 2, mixing the cDNA obtained with the oligonucleotides as set forth in SEQ ID NO: 3 to SEQ ID NO: 8 and buffer comprising reagents used for DNA amplification to obtain a reaction mixture, incubating said reaction mixture at a substantial temperature for a substantial period of time and detecting amplified product, wherein presence of the amplified products confirms presence of the virus.

Yet another aspect of the present invention provides a kit for detection of Swine Flue Virus H1 type comprising the oligonucleotides as set forth in SEQ ID NO: 3 to SEQ ID NO: 8.

BRIEF DESCRIPTION OF THE ACCOMPANYING DRAWINGS

FIG. 1 shows SyBR Green-I fluorescent dye mediated monitoring of Swine Flu H1 specific isothermal gene amplification assay. A. Naked eye inspection under normal light. The original orange color of the SYBR Green-I changed to yellow in case of positive amplification whereas in negative control having no amplification, the original orange color is retained. B. The visual observation of green fluorescence of DNA binding SYBR Green-I under ultraviolet light.

Figure 2:
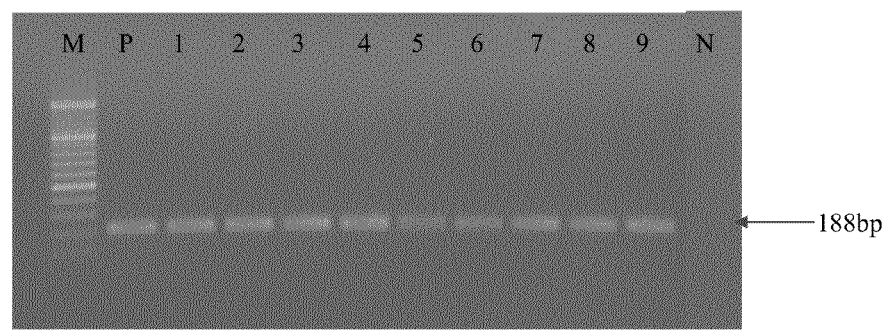
Figure 3:
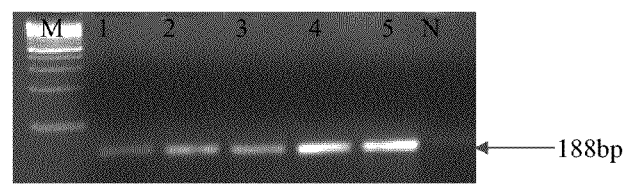

FIG. 2 shows Agarose gel electrophoresis of Real time PCR products of swine flu H1 gene assay additional positive samples
Lane M: Fermantas 100 bp DNA Ladder
Lane P: Positive control
Lane 1-9: additional positive samples
Lane N: Negative control FIG. 3 shows Real time PCR of swine flu H1 gene amplification assay for CDC Seasonal flu samples using F3-B3 Primers
Agarose gel electrophoresis of Real time PCR products of swine flu H1 gene amplification assay for CDC seasonal flu positive additional picked samples
Lane M: Fermantas 100 bp DNA Ladder
Lane 1-5: additional positive samples
Lane N: Negative control

DETAILED DESCRIPTION OF THE INVENTION

As used herein the term "amplified" or "amplification" refers to the production of many DNA copies from one or few copies of template DNA.

As used herein the term "biological sample" includes but is not limited to nasopharyngeal swab, nasal swab, throat swab, combined oropharyngeal/nasopharyngeal swab, nasal aspirate, serum, plasma, semen, urine, or blood.

As used herein, the term "oligonucleotide" or "primer" refers to a series of linked nucleotide residues, which oligonucleotide has a sufficient number of nucleotide bases to be used in a polymerase chain reaction. A short oligonucleotide sequence may be based on or designed from a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. Oligonucleotides of the invention can be chemically synthesized and can be used as probes.

As used herein, the term "probes" refer to nucleic acid sequences of variable length, preferably between at least about 10 nt or about 100 nt depending on use. Probes are used in the detection of identical, similar, or complementary nucleic acid sequences. Longer length probes are usually obtained from a natural or recombinant source, are highly specific and much slower to hybridize than oligomers. Probes may be single or double stranded and designed to have specificity in PCR, membrane-based hybridization technologies, or ELISA-like technologies, preferably PCR, more preferably RT-PCR, and even more preferably in real-time RT-PCR.

In the current pandemic scenario, confirmation of pandemic H1N1 influenza A infection can only be made by using WHO approved CDC recommended real-time reverse-transcriptase (RT)-PCR based on Taqman chemistry using a panel of oligonucleotide primers and dual labeled hydrolysis probe employing invitrogen Super script™ III Platinum ®one step quantitative kit with four sets of primer and probes for Universal Influenza A, Swine Influenza A, Swine H1(New H1N1), House Keeping gene (RNase P) for testing the quality of RNA template (United States Centers for Disease Control and Prevention. Interim Guidance for the Detection of Novel Influenza A virus Using Rapid Influenza Diagnostic Tests with reference to Swine Flu H1N1 virus, http://wwvv.cdc.gov/hInlflu/guidance/rapid_testing.htm Accessed Aug. 4, 2009).

One of the limitations of the existing WHO approved CDC recommended real-time RT-PCR is that the test system is very expensive considering the large number of primer and probe sets employed.

Another limitation of the WHO approved CDC recommended real-time RT-PCR is the requirement of expensive real-time PCR equipment ($50,000) that can be affordable only by referral laboratories with good financial resources.

Still another limitation of real-time RT-PCR test system is that the process fore detection of Swine Flu virus known in the prior art is time consuming as it requires 3-4 hours.

Further limitation of real-time RT-PCR is the limited availability of reagents and technical expertise required for performance and interpretation make it out of bound for routine laboratory diagnosis.

Thereafter, real-time RT-PCR is not the method of choice for clinical diagnosis of novel H1N1 virus due to the requirement of sophisticated instrumentation and expensive reagents. It is therefore there is a need to provide a quick, simple, sensitive and economical assay tests that can be used in field conditions especially at peripheral healthcare settings as a routine test without requirement of any sophisticated high end equipments.

In accordance with the present invention in one of the embodiment of the present invention there is provided a rapid, simple, sensitive and cost effective Swine flu virus H1 specific isothermal gene amplification assay employing highly specific and sensitive oligonucleotides for reliable and early clinical diagnosis of H1N1 in a sample.

The present invention also provides oligonucleotides useful as primers and probes.

In one embodiment of the present invention there is provided an oligonucleotide set for detection of Swine Flue Virus H1 type in a sample, the set comprises the oligonucleotides as set forth in SEQ ID NO: 3 to SEQ ID NO: 8.

In one embodiment of the present invention there is provided a process of obtaining cDNA from a sample containing Swine Flu virus H1 type using the oligonucleotides as set forth in SEQ ID NO: 1 and SEQ ID NO: 2.

In another embodiment of the present invention provides a process for detecting Swine Flu Virus H 1 type in a sample, the process comprises providing the sample, mixing the sample with the oligonucleotides as set forth in SEQ ID NO: 3 to SEQ ID NO: 8 and buffer comprising reagents used for DNA amplification to obtain a reaction mixture, incubating the reaction mixture at a substantial temperature for a substantial period of time and detecting the amplified product, wherein presence of the amplified products confirms presence of the virus.

In yet another embodiment of the present invention there is provided a process of detection of Swine Flu Virus H1 type in a sample, wherein the process comprises providing the sample, obtaining cDNA from the sample using oligonucleotides as set forth in SEQ ID NO: 1 and SEQ ID NO: 2, mixing the cDNA obtained with the oligonucleotides as set forth in SEQ ID NO: 3 to SEQ ID NO: 8 and buffer comprising reagents used for DNA amplification to obtain a reaction mixture, incubating the reaction mixture at a substantial temperature for a substantial period of time and detecting amplified product, wherein presence of the amplified products confirms presence of the virus.

In yet another embodiment of the present invention there is provided a process of detection of Swine Flu Virus H1 type in a sample, wherein the process comprises providing the sample, obtaining cDNA from the sample using oligonucleotides as set forth in SEQ ID NO: 1 and SEQ ID NO: 2, mixing the cDNA obtained with the oligonucleotides as set forth in SEQ ID NO: 3 to SEQ ID NO: 8 and buffer comprising reagents used for DNA amplification to obtain a reaction mixture, incubating the reaction mixture at a temperature ranging from 60° C. to 65° C. preferably at 65° C. for 15 minutes to 45 minutes preferably 30 minutes and detecting amplified product, wherein presence of the amplified products confirms presence of the virus.

In yet another embodiment of the present invention, there is provided a process for detecting Swine flu virus H1 type in a sample, the process comprising providing the sample containing Swine flu virus H1 type DNA, mixing the sample with the oligonucleotides as set forth in SEQ ID NO: 3 to SEQ ID NO: 8 and buffer comprising reagents used for DNA amplification to obtain a reaction mixture, incubating the reaction mixture at a temperature ranging from about 60° C. to 65° C. for a substantial period of time and detecting the amplified product, wherein presence of the amplified products confirms presence of the virus.

In yet another embodiment of the present invention, there is provided a process for detecting Swine flu virus H1 type in a sample, the process comprising providing the sample containing Swine flu virus H1 type DNA, mixing the sample with the oligonucleotides as set forth in SEQ ID NO: 3 to SEQ ID NO: 8 and buffer comprising reagents used for DNA amplification to obtain a reaction mixture, incubating the reaction mixture at a temperature ranging from about 60° C. to 65° C. for 15 to 45 minutes and detecting the amplified product, wherein presence of the amplified products confirms presence of the virus.

In yet another embodiment of the present invention, there is provided a process for detecting Swine flu virus H1 type in a sample, the process comprising providing the sample, mixing the sample with the oligonucleotides as set forth in SEQ ID NO: 3 to SEQ ID NO: 8 and buffer comprising reagents used for DNA amplification to obtain a reaction mixture, incubating the reaction mixture at 63° C. for a substantial period of time and detecting the amplified product, wherein presence of the amplified products confirms presence of the virus.

In another embodiment of the present invention provides a process for detecting Swine flu virus H1 type in a sample, the process comprising providing the sample, mixing the sample with the oligonucleotides as set forth in SEQ ID NO: 3 to SEQ ID NO: 8 and buffer comprising reagents used for DNA amplification to obtain a reaction mixture, incubating the reaction mixture at a substantial temperature for 15 minutes to 45 minutes and detecting the amplified product, wherein presence of the amplified products confirms presence of the virus.

In another embodiment of the present invention provides a process for detecting Swine flu virus H1 type in a sample, the process comprising providing the sample, mixing the sample with the oligonucleotides as set forth in SEQ ID NO: 3 to SEQ ID NO: 8 and buffer comprising reagents used for DNA amplification to obtain a reaction mixture, incubating the reaction mixture at 63° C. temperature for 30 minutes and detecting the amplified product, wherein presence of the amplified products confirms presence of the virus.

In another embodiment of the present invention provides a process for detecting Swine flu virus H1 type in a sample, wherein the amplified product is detected by checking turbidity of the sample, wherein formation of turbidity indicates presence of Swine Flue Virus H1 type DNA in the sample.

In another embodiment of the present invention provides a process for detecting Swine flu virus H1 type in a sample, wherein the amplified product is detected by SYBR Green I dye assay.

In another embodiment of the present invention provides a process for detecting Swine flu virus H1 type in a sample, wherein the amplified product is detected by SYBR Green I dye assay.

In yet another embodiment of the present invention, there is provided a process for detecting Swine flu virus H1 type in a sample, the process comprising providing the sample containing Swine flu virus H1 type DNA, mixing the sample with the oligonucleotides as set forth in SEQ ID NO: 3 to SEQ ID NO: 8 and buffer comprising reagents used for DNA amplification to obtain a reaction mixture, incubating the reaction mixture at a substantial temperature for a substantial period of time, and detecting the amplified product following adding SYBR Green I dye to the incubated reaction mixture, wherein presence of green color confirms presence of the amplified products and thus confirms presence of the virus.

In yet another embodiment of the present invention there is provided a process of detection of Swine Flu Virus H1 type in a sample, wherein the process comprises providing the sample, obtaining cDNA from the sample using oligonucleotides as set forth in SEQ ID NO: 1 and SEQ ID NO: 2, mixing the cDNA obtained with the oligonucleotides as set forth in SEQ ID NO: 3 to SEQ ID NO: 8 and buffer comprising reagents used for DNA amplification to obtain a reaction mixture, incubating the reaction mixture at a temperature ranging from 60° C. to 65° C. preferably at 65° C. for 15 minutes to 45 minutes preferably 30 minutes and detecting the amplified product following adding SYBR Green I dye to the incubated reaction mixture, wherein presence of green color confirms presence of the amplified products and thus confirms presence of the virus.

In further embodiment of the present invention there is provided a kit for detection of Swine Flue Virus H1 type comprising oligonucleotides as set forth in SEQ ID NO: 1 to SEQ ID NO: 8.

In further embodiment of the present invention there is provided a kit for detection of Swine Flue Virus H1 type comprising oligonucleotides as set forth in SEQ ID NO: 3 to SEQ ID NO: 8.

In a particular embodiment, the present invention provides an isothermal gene amplification assay for the simple and fast diagnosis of swine flu patients.

In one embodiment of the present invention there are provided oligonucleotides as set forth in SEQ ID NO: 1 to 8.

In another embodiment, the invention encompasses methods for detection of swine flu virus in a biological sample using isothermal gene amplification technique, the method comprising amplifying HA gene of H1N1 virus in the sample using oligonucleotides as set forth in SEQ ID NO: 3 to SEQ ID NO: 8.

The result can be monitored either in the form of turbidity or change of color through naked eye. The better appreciation of apple green fluorescence can be achieved by UV hand held torch.

Another embodiment of the invention encompasses a rapid method of detection of swine flu virus oligonucleotides as set forth in SEQ ID NO: 3 to SEQ ID NO: 8, wherein the result can be obtained in 60 min as compared to 3-4 hour by conventional gene amplification assays. The method is very simple and obviates the need of expensive high end equipment such as Real-time PCR machine which is very expensive ($40000-$50000).

The process of detection of swine flu virus disclosed in the present invention provide high sensitivity of the technique that can detect very low copy number of viruses especially in those borderline cases that will be missed by conventional RT-PCR techniques.

This is an alternate real-time test system for rapid detection as well as identification of novel H1N1 Swine Flu virus. The assay is based on a simple isothermal gene amplification tool using a specially designed primer set that specifically amplify the H1 gene of novel H1N1 Swine Flu virus only. The comparative evaluation with CDC recommended real-time RT-PCR with limited number of samples revealed 100% concordance. The higher sensitivity and specificity of the reaction is attributed to continuous amplification under isothermal condition employing six primers recognizing eight distinct regions of the target. One of the most attractive features of this isothermal gene amplification assay seems to have great advantage in terms of monitoring of amplification that can be accomplished by SYBR Green I dye mediated naked eye visualization. The reported isothermal gene amplification method will be rapid and cost effective since gene amplification can be accomplished in a heating block/water bath followed by monitoring of gene amplification through visual fluorescence in the form of colour change by naked eye within 1 hour. These simple attributes of Isothermal gene amplification assay favors it to be adopted as a field gene amplification technology without requiring any expensive equipments.

The present invention provides SYBR Green I based isothermal gene amplification assay for rapid detection of H1N1 Swine Flu virus nucleic acid in clinical specimens by targeting the structural HA gene. The particular importance is the substantial reduction in time required for the confirmation of results in 1 hr as compared to 3-4 hours in case of real time RT-PCR.

In one of the embodiment there is provided a process of identification of swine Flu Virus H1 type in a sample, wherein the process comprising providing a sample, reverse transcribing the RNA of present in the sample into cDNA using backward outer primer as set forth in SEQ ID NO: 1 and SEQ ID NO: 2 and amplifying the resultant cDNA by mixing of the buffer, oligonucleotide as set forth in SEQ ID NO: 3 to SEQ ID NO: 8, DNA polymerase at a temperature ranging from about 60° C. to 65° C. preferably 63° C. for about 15 minutes to 45 minutes preferably 30 minutes; and detecting the amplified product, wherein presence of the amplified products confirms presence of the virus.

In one of the embodiment there is provided a process of identification of swine Flu Virus H1 type in a sample, wherein the process comprising providing a sample, reverse transcribing the RNA of present in the sample into cDNA using backward outer primer as set forth in SEQ ID NO: 1 and SEQ ID NO: 2 and amplifying the resultant cDNA by mixing of the buffer, oligonucleotide as set forth in SEQ ID NO: 3 to SEQ ID NO: 8, DNA polymerase at a temperature ranging from about 60° C. to 65° C. preferably 63° C. for about 15 minutes to 45 minutes preferably 30 minutes; and detecting the amplified product following adding SYBR Green I dye to the incubated reaction mixture, wherein presence of green color confirms presence of the amplified products and thus confirms presence of the virus.

The isothermal gene amplification assay disclosed in the present invention is a simple and quick diagnostic tool, wherein the process comprises reverse transcribing the RNA template into cDNA with oligonucleotides as set forth in SEQ ID NO: 1 and SEQ ID NO: 2 and amplification of the resultant cDNA by mixing of the buffer, oligonucleotide as set forth in SEQ ID NO: 3 to 8, DNA polymerase, and incubating the mixture at 63° C. for 30 minutes.

Advantages of the Invention

The present invention discloses one step single tube isothermal RTLAMP gene amplification assay for rapid detection of novel S-OIV H1N1 virus. The process of detection of Swine flu as disclosed in the present invention is real-time test system for rapid detection as well as identification of novel S-OIV H1N1 virus.

The Swine flu Virus Type 1 detection process disclosed in the present invention is specific and highly sensitive and provides accurate results and does not result any cross amplification, negating the possibilities of false positive results and detects low copy number of viruses DNA especially in those borderline cases that will be missed by conventional RT-PCR techniques.

The oligonucleotides disclosed in the present invention are highly specific that amplifies only Swine Flu Virus Type 1 (H1N1) and not the Seasonal Flu (Influenza A).

The process of detection of Swine flu virus type 1 disclosed in the present invention is sensitive, simple, rapid and cost effective gene amplification technique that can be used in a routine diagnostic laboratory as well as in peripheral health care centers for clinical diagnosis of Swine Flu (H1N1) patients.

Further, the detection process of the present invention obviates the need of expensive high end equipment such as Real-time PCR machine which is very expensive ($40000-$50000).

The detection process of the present invention is rapid where the result can be obtained in 60 min as compared to 3-4 hour by conventional gene amplification assays.

One of the most important features of the isothermal gene amplification assay as disclosed in the present invention has great advantage in terms of monitoring of amplification that can be accomplished by SYBR Green I dye mediated naked eye visualization.

The disclosed assay is rapid and cost effective since gene amplification can be accomplished in a heating block/water bath followed by monitoring of gene amplification through visual fluorescence in the form of colour change by naked eye.

These simple attributes of the assay favors it to be adopted as a field gene amplification technology without requiring any expensive instrument.

The process is very simple and obviates the need of expensive high end equipment such as Real-time PCR instrument which is very expensive.

The process is based on a simple isothermal gene amplification tool using a specially designed primer set that specifically amplify the H1 gene of novel S-OIV only. Unlike PCR where the target gene is flanked by two primers, in case of LAMP, a set of six primers flank a small target of approximately 200 by through recognition of eight different sequences of the target gene. Hence LAMP amplification is very selective and target specific.

The process is highly sensitive and specific that can detect very low copy number of viruses especially in those borderline cases that will be missed by conventional RT-PCR techniques.

Oligonucleotides

A set of six oligonucleotides (SEQ ID NO: 1-8) comprising two outer, two inner and two loop oligonucleotides that recognize eight distinct regions spanning over 188 by conserved regions of structural HA gene of novel H1N1 virus corresponding to the genome position 529-716 was designed. The two outer primers were described as forward outer primer (F3, SEQ ID NO: 1) and backward outer primer (B3, SEQ ID NO: 2). The inner primers were described as forward inner primer (FIP, SEQ ID NO: 3) and backward inner primer (BIP, SEQ ID NO: 4). Further, two loop primers viz; forward loop primer (FLP, SEQ ID NO: 5) and backward loop primer (BPL, SEQ ID NO: 6) were designed to accelerate the amplification reaction. The usefulness of the selected primer set is to detect all strains/isolates of H1N1 swine flu virus with high sensitivity and specificity. It was established through sequence alignment of all available HA gene sequences in the GenBank including the circulating strains in India responsible for recent pandemic using DNASIS software. The details of the primer sequences with regard to genome position are depicted in Table 1.

EXAMPLES

The disclosure will now be illustrated with working examples, which is intended to illustrate the working of disclosure and not intended to take restrictively to imply any limitations on the scope of the present disclosure.

Example 1

RNA extraction of cDNA Preparation

The genomic viral RNA was extracted from 140 µl of suspected human patient serum using QIAamp viral RNA mini kit (QIAGEN, Germany), according to the manufacturer's protocols. The eluted RNA was then reverse transcribed to cDNA in a 10 µl reaction volume by incubating 2 µl of RNA with 10 pmole of B3 (Backward primer) in 2 µl of 5× buffer, 1 µl of 10 mM dNTP mix and 0.25 µl of 200 U/µl MMLV-RT, 0.25 µl of RNasin inhibitor and 3.5 µl of nuclease free water at 37° C. for 30 min.

Example 2

Gene Amplification

The amplification of HA gene of H1N1 virus was carried out in a total 25 µl reaction volume using the in-house buffer comprising 20 mM Tris-HCL pH8.8, 10 mM KCI, 10 mM $(NH_4)_2SO_4$, 8 mM $MgSO_4$, 1.4 mM dNTPs, 0.8 M Betaine, 0.1% Tween-20 with 50 pmol each of the primers FIP and BIP, 5 pmol each of the outer primers F3 and B3, 25 pmol each of loop primers FLP and BLP, 8 units of the Bst DNA polymerase (New England Biolabs), The gene amplification was accomplished by incubating the reaction mixture at 63° C. for 30 min in routine laboratory water bath/dry heating bath.

Example 3

Visualization of Gene Amplification

The monitoring of gene amplification was carried out with naked eye visual inspection. Following amplification, the tubes were inspected for white turbidity through naked eye after a pulse spin to deposit the precipitate in the bottom of the tube. The inspection for amplification was also performed through observation of color change following addition of 0.5 µl of SYBR Green I dye to the tube. In case of positive amplification, the original orange color of the dye will change into green that can be judged under natural light as well as under UV light (302 nm) with the help of a hand held UV torch lamp. In case there is no amplification, the original orange color of the dye will be retained (FIG. 1). This change of color is permanent and thus can be kept for record purpose.

Example 4

Validation with Patient Throat Swab Samples

The applicability of this modified SYBR Green I based isothermal gene amplification assay for clinical diagnosis was validated with 20 suspected human patient throat swab samples including 5 seasonal flu and 4 healthy Throat/nasal samples as negative control. The results were compared with WHO approved CDC recommended Real-Time RT-PCR. The isothermal gene amplification assay has demonstrated excellent sensitivity and specificity by correctly picking up the entire 11 CDC real-time PCR positive sample (FIGS. 2 and 3; Table 2). Further no cross reaction was observed with seasonal flu as well as healthy throat/nasal swab samples thereby establishing the specificity of the reported gene amplification technique for novel H1N1 swine flu virus only.

It was confirmed that the samples which are confirmed as seasonal flu samples using WHO approved CDC recommended Real-Time RT-PCR are actually positive for H1N1 strain when tested using the process of detection of swine flu virus using the primers as disclosed in the present invention. This shows the sensitivity and 100% accuracy of the primer disclosed in the present invention.

TABLE 1

Details of primer sets designed for rapid detection of novel Swine Flu H1N1 virus* strain

| SEQ ID NOs | Name of the Primer | Genome Position* | Length (bp) | Sequence Details |
|---|---|---|---|---|
| SEQ ID NO: 1 | Forward Outer (F3) | 529-547 | 19 | AAGCTCAGCAAATCCTACA |
| SEQ ID NO: 2 | Backward Outer (B3) | 699-716 | 18 | TCCCTCACTTTGGG TCTT |
| SEQ ID NO: 3 | Forward Inner primer (FIP) | Flc 598-622 | 25 | GACTTTGTTGGTCAGCACTAGTAGA |
| SEQ ID NO: 4 | [Flc + TTTT + F2] | F2 556-574 | 19 | AAAGGGAAAGAAGTCCTCG |
| SEQ ID NO: 5 | Backward Inner primer (BIP) | B1 623-647 | 25 | TCTATCAGAATGCAGATGCATATGT |
| SEQ ID NO: 6 | [B1 + TTTT + B2c] | B2 679-696 | 18 | TGCTATTTCCGGCTTGAA |
| SEQ ID NO: 7 | Forward Loop Primer (FLP) | 576-595 | 20 | GATGGTGAATGCCCCATAGC |
| SEQ ID NO: 8 | Backward Loop Primer (BLP) | 650-672 | 23 | TTGTGGGGTCATCAAGATACAGC |

(*Gen Bank Accession No-FJ966082; WHO recommended referral strain)

TABLE 2

Comparative evaluation of Swine Flu H1 specific isothermal gene amplification assay and WHO approved CDC recommended Real-time RT-PCR assay for the detection of HA gene of H1N1 virus in suspected Human patient throat swab samples

| Sample Type | Number of samples | CDC Real-Time RT-PCR | Isothermal gene amplification assay |
|---|---|---|---|
| Sample Flu (H1N1) | 11 | H1N1 positive | H1N1 positive |
| Seasonal Flu (Influenza A) | 5 | Influenza A Positive | H1N1 positive |
| Negative (Throat swab samples from healthy individuals) | 4 | 0 | 0 |

We claim:

1. A process for detecting pandemic Swine flu virus H1N1 type in a sample, said process comprises providing the sample, mixing the sample with the oligonucleotides as set forth in SEQ ID NO: 1 to SEQ ID NO: 8 and buffer comprising reagents used for RNA amplification to obtain a reaction mixture, incubating said reaction mixture at a temperature of about 60° C. to about 65° C. for a period of about 15 minutes to about 45 minutes and detecting amplified product, wherein presence of the amplified products confirms presence of the virus.

2. A process of detecting pandemic Swine Flu Virus H1N1 type in a sample, wherein said process comprises providing the sample, obtaining cDNA from the sample using oligonucleotides as set forth in SEQ ID NO: 1 and SEQ ID NO: 2, mixing the cDNA obtained with the oligonucleotides as set forth in SEQ ID NO: 3 to SEQ ID NO: 8 and buffer comprising reagents used for DNA amplification to obtain a reaction mixture, incubating said reaction mixture at a temperature of about 60° C. to about 65° C. for a period of about 15 minutes to about 45 minutes and detecting amplified product, wherein presence of the amplified products confirms presence of the virus.

3. The process as claimed in claim 1 or 2, wherein the temperature is about 63° C.

4. The process as claimed in claim 1 or 2, wherein the period is about 30 minutes.

5. The process as claimed in claim 1 or 2, wherein the amplified product is detected by checking turbidity of the sample, wherein formation of turbidity indicates the presence of Swine Flu Virus H1N1 type DNA in the sample.

6. The process as claimed in claim 1 or 2, wherein the amplified product is detected by a SYBR Green I dye assay.

7. A primer set for detection of pandemic Swine Flu Virus H1N1 type in a sample comprising:
    (a) a forward outer primer (F3) comprising the oligonucleotide of SEQ ID NO:1 and
    (b) a backward outer primer (B3) comprising the oligonucleotide of SEQ ID NO:2 a forward inner primer (FIP) comprising the oligonucleotide of SEQ ID NO:3, a linker and the oligonucleotide of SEQ ID NO:4;
    (c) a backward inner primer (BIP) comprising the oligonucleotide of SEQ ID NO:5, a linker and the oligonucleotide of SEQ ID NO:6;
    (d) a forward loop primer (FLP) comprising the oligonucleotide of SEQ ID NO:5; and
    (e) a backward loop primer (BLP) comprising the oligonucleotide of SEQ ID NO: 8.

8. The primer set as claimed in claim 7, wherein the linker is a TTTT tetra linker.

* * * * *